(12) United States Patent
Hanning et al.

(10) Patent No.: US 10,269,454 B2
(45) Date of Patent: Apr. 23, 2019

(54) METHOD OF CONFIGURING DEVICES IN AN OPERATING THEATER

(71) Applicant: Stryker Corporation, Kalamazoo, MI (US)

(72) Inventors: Steven Michael Hanning, Ben Lomond, CA (US); Ramanan Paramasivan, San Jose, CA (US); Brian D. Bailey, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 239 days.

(21) Appl. No.: 14/982,636

(22) Filed: Dec. 29, 2015

(65) Prior Publication Data
US 2016/0196400 A1 Jul. 7, 2016

Related U.S. Application Data

(60) Provisional application No. 62/100,286, filed on Jan. 6, 2015.

(51) Int. Cl.
*G16H 40/63* (2018.01)
*G06F 19/00* (2018.01)
*G06F 9/445* (2018.01)

(52) U.S. Cl.
CPC ......... *G16H 40/63* (2018.01); *G06F 9/44505* (2013.01); *G06F 19/00* (2013.01)

(58) Field of Classification Search
CPC ................ G06F 19/3406; G06F 9/44505
USPC ........................................ 713/100
See application file for complete search history.

(56) References Cited

U.S. PATENT DOCUMENTS

| | | | |
|---|---|---|---|
| 3,960,140 A | 6/1976 | Buxton | |
| 4,051,522 A | 9/1977 | Healy et al. | |
| 4,933,843 A | 6/1990 | Scheller et al. | |
| 4,958,645 A | 9/1990 | Cadell et al. | |
| 5,319,363 A | 6/1994 | Welch et al. | |
| 5,579,775 A | 12/1996 | Dempsey et al. | |

(Continued)

FOREIGN PATENT DOCUMENTS

| | | | |
|---|---|---|---|
| EP | 0 505 627 A2 | 9/1992 | |
| EP | 0 602 459 A2 | 6/1994 | |

(Continued)

OTHER PUBLICATIONS

U.S. Appl. No. 62/061,398, filed Oct. 8, 2014; Intra-Surgical Documentation System; Applicant: Steven Michael Hanning.

(Continued)

*Primary Examiner* — Alina A Boutah
(74) *Attorney, Agent, or Firm* — Morrison & Foerster, LLP

(57) ABSTRACT

A method of configuring an operating room including providing a storage system having system preferences, providing an operating room communicator, connecting at least one configurable device to the operating room communicator, obtaining the system preferences from the storage system, and configuring settings of the at least one configurable device according to the system preferences. The system preferences can be obtained without logging into the storage system. The system preferences can also be obtained when a surgeon comes into proximity with the operating room communicator without actively interacting with the operating room communicator.

16 Claims, 9 Drawing Sheets

(56) References Cited

U.S. PATENT DOCUMENTS

| | | | |
|---|---|---|---|
| 5,594,786 A | 1/1997 | Chaco et al. | |
| 5,682,529 A * | 10/1997 | Hendry | G06F 3/14 |
| | | | 710/16 |
| 5,687,734 A | 11/1997 | Dempsey et al. | |
| 5,738,102 A | 4/1998 | Lemelson | |
| 5,740,801 A | 4/1998 | Branson | |
| 5,748,103 A | 5/1998 | Flach et al. | |
| 5,767,791 A | 6/1998 | Stoop et al. | |
| 5,877,819 A | 3/1999 | Branson | |
| 5,907,291 A | 5/1999 | Chen et al. | |
| 5,960,085 A | 9/1999 | de la Huerga | |
| 6,213,942 B1 | 4/2001 | Flach et al. | |
| 6,314,297 B1 | 11/2001 | Karl | |
| 6,344,794 B1 | 2/2002 | Ulrich et al. | |
| 6,402,737 B1 | 6/2002 | Tajima et al. | |
| 6,574,742 B1 * | 6/2003 | Jamroga | G06F 17/3028 |
| | | | 705/2 |
| 6,600,421 B2 | 7/2003 | Freeman | |
| 6,876,303 B2 | 4/2005 | Reeder et al. | |
| 7,289,825 B2 | 10/2007 | Fors et al. | |
| 7,343,403 B2 * | 3/2008 | Komiya | H04L 41/0846 |
| | | | 707/999.01 |
| 7,711,324 B2 * | 5/2010 | Wutka | G06F 3/038 |
| | | | 455/41.2 |
| 7,846,150 B2 | 12/2010 | Hamel et al. | |
| 7,883,458 B2 | 2/2011 | Hamel | |
| 7,890,743 B2 * | 2/2011 | Buchanan | G06F 15/16 |
| | | | 340/539.23 |
| 8,149,108 B2 | 4/2012 | Hamel et al. | |
| 8,175,590 B2 | 5/2012 | Hamel et al. | |
| 8,638,191 B2 | 1/2014 | Hamel et al. | |
| 9,035,741 B2 | 5/2015 | Hamel et al. | |
| 2002/0013518 A1 | 1/2002 | West et al. | |
| 2003/0025604 A1 | 2/2003 | Freeman | |
| 2003/0093503 A1 | 5/2003 | Yamaki et al. | |
| 2005/0035862 A1 | 2/2005 | Wildman et al. | |
| 2005/0216311 A1 * | 9/2005 | Gmelin | G06F 19/322 |
| | | | 705/3 |
| 2006/0047793 A1 * | 3/2006 | Agrawal | H04L 41/0843 |
| | | | 709/221 |
| 2006/0116667 A1 | 6/2006 | Hamel et al. | |
| 2006/0253441 A1 * | 11/2006 | Nelson | G06F 17/30722 |
| 2008/0256076 A1 * | 10/2008 | Claus | G06F 19/3406 |
| 2008/0281301 A1 * | 11/2008 | DeBoer | A61B 17/00 |
| | | | 606/1 |
| 2008/0303707 A1 | 12/2008 | Larsen et al. | |
| 2009/0300507 A1 | 12/2009 | Raghavan et al. | |
| 2010/0287127 A1 * | 11/2010 | Claus | A61F 9/00745 |
| | | | 706/12 |
| 2012/0010904 A1 * | 1/2012 | Buck | G06F 19/327 |
| | | | 705/3 |
| 2012/0173257 A1 * | 7/2012 | Preiss | G06Q 10/06 |
| | | | 705/2 |
| 2012/0271650 A1 * | 10/2012 | Ahn | G06Q 50/22 |
| | | | 705/2 |
| 2013/0208966 A1 * | 8/2013 | Zhao | G06F 9/5072 |
| | | | 382/131 |
| 2013/0231955 A1 * | 9/2013 | De Villiers | G06F 19/363 |
| | | | 705/3 |
| 2013/0267779 A1 | 10/2013 | Woolford et al. | |
| 2015/0223692 A1 * | 8/2015 | Snichelotto | A61N 1/37211 |
| | | | 600/510 |
| 2016/0100788 A1 * | 4/2016 | Sano | A61B 5/6898 |
| | | | 600/595 |

FOREIGN PATENT DOCUMENTS

| | | |
|---|---|---|
| EP | 1 038 497 A1 | 9/2000 |
| EP | 1 414 337 B1 | 5/2004 |
| WO | WO 01/85085 A2 | 11/2001 |

OTHER PUBLICATIONS

"Val Med Goes National"; Author unknown; ICT Infection Control Today; article dated Mar. 17, 2000 (3 pages).

* cited by examiner ively adjust the settings for each device in the operative theater before surgery. An easier method of adjusting the settings of devices in an operative theater is desired.
METHOD OF CONFIGURING DEVICES IN AN OPERATING THEATER

CROSS REFERENCE TO RELATED APPLICATION

This claims the benefit of U.S. Provisional Application Ser. No. 62/100,286, filed Jan. 6, 2015, which is incorporated herein by reference in its entirety.

FIELD OF THE INVENTION

The present invention relates to a method of configuring devices in an operating theater.

BACKGROUND OF THE INVENTION

Surgeons use many devices to help them during operative procedures. In the past, surgeons or other people in the operative theater have had to individually adjust the settings for each device in the operative theater before surgery. An easier method of adjusting the settings of devices in an operative theater is desired.

SUMMARY OF THE INVENTION

The present invention, according to one aspect, is directed to a method of configuring an operating room comprising providing a storage system having system preferences, providing an operating room communicator, connecting at least one configurable device to the operating room communicator, obtaining the system preferences from the storage system, and configuring settings of at least one configurable device according to the system preferences. The system preferences can be obtained without logging into the storage system. The system preferences can also be obtained when a surgeon comes into proximity with the operating room communicator without actively interacting with the operating room communicator.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

For purposes of description herein, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
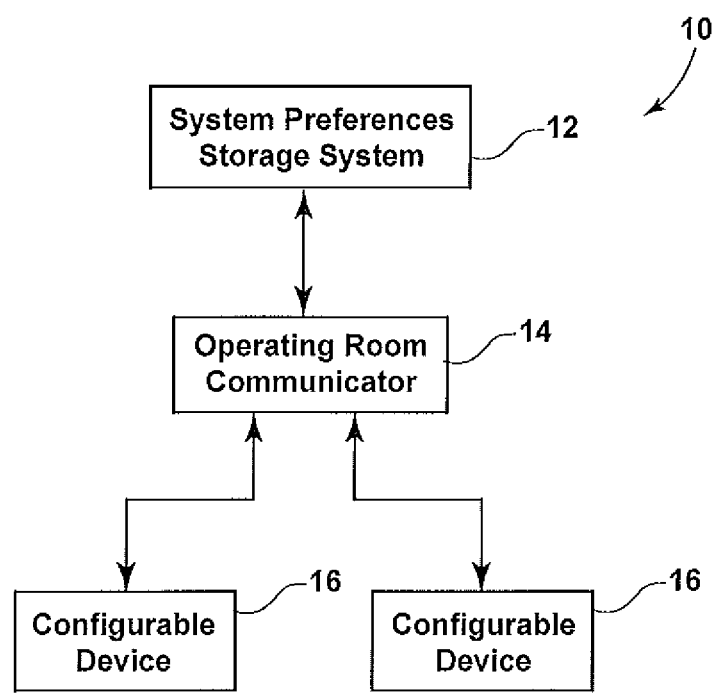
FIG. 1 is a schematic view of a system for configuring devices in an operating room embodying an aspect of the present invention.

The reference number 10 (FIG. 1) generally designates a schematic of a system 10 for configuring devices in an operating room 100 (FIG. 9) embodying an aspect of the present invention. The system 10 includes a plurality of configurable devices 16 located within the operating room 100. The configurable devices 16 have settings that can be configured depending on the preferences of at least one person (typically located within the operating room (e.g., a surgeon and/or a nurse)). In the illustrated example, the configurable devices 16 communicate with an operating room communicator 14, which in turn communicates with a system preference storage system 12. Once the operating room communicator 14 obtains the preferences for the configurable devices 16 from the system preference storage system 12, the operating room communicator 14 communicates with the configurable devices 16 to configure the settings thereof according to the preferences of at least one person in the operating room. The operating room communicator 14 obtains the preferences for the configurable devices 16 without logging into the system preference storage system 12. As used here, "logging into" means a process by which individual access to a computer system or database is controlled by identifying and authenticating the user through credentials presented by the user. According to the present embodiment, the user (e.g., the person in the operating room) does not have to be authenticated through credentials to obtain the preferences for the settings of the configurable devices 16.

Figure 2:
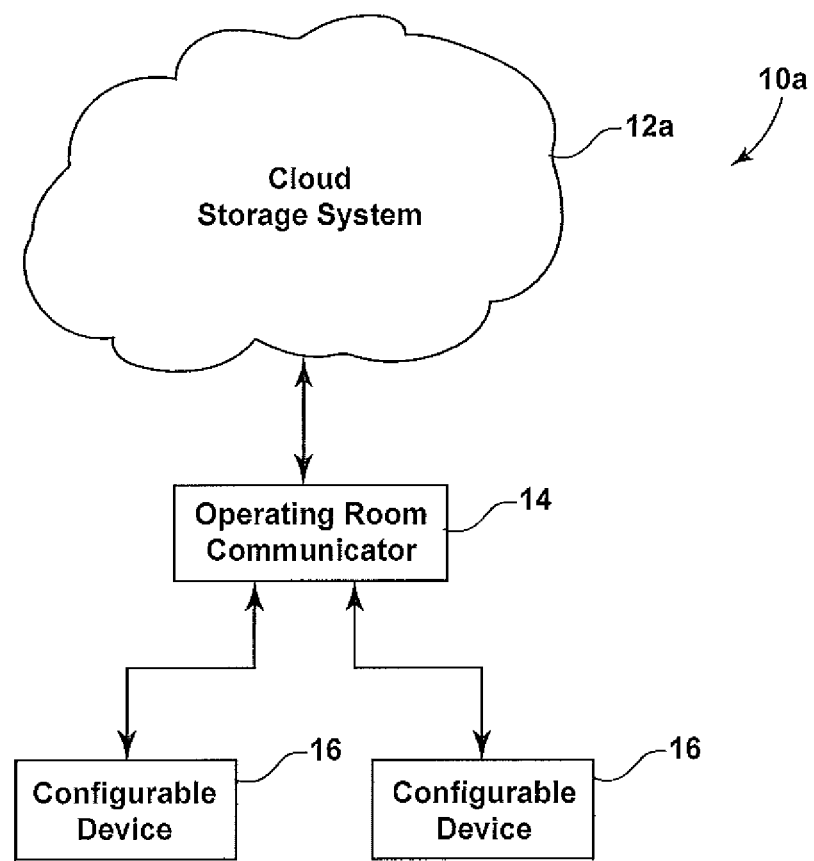
FIG. 2 illustrates a first embodiment of the system for configuring devices in the operating room, wherein the system preference storage system is a cloud storage system.

FIG. 2 illustrates a first embodiment of the system 10a for configuring devices in the operating room 100, wherein the system preference storage system 12 is a cloud storage system 12a. As illustrated in FIG. 2, the operating room communicator 14 communicates with the cloud storage system 12a. The cloud storage system 12a can be shared by several organizations and can be managed by the organizations or a third party and may exist on-premises or off-premises. The cloud storage system 12a has an index of surgeons and system preferences associated with each surgeon in the index of surgeons. The system preferences include the preferences for the settings of the configurable devices 16 in the operating room 100.

Figure 3:
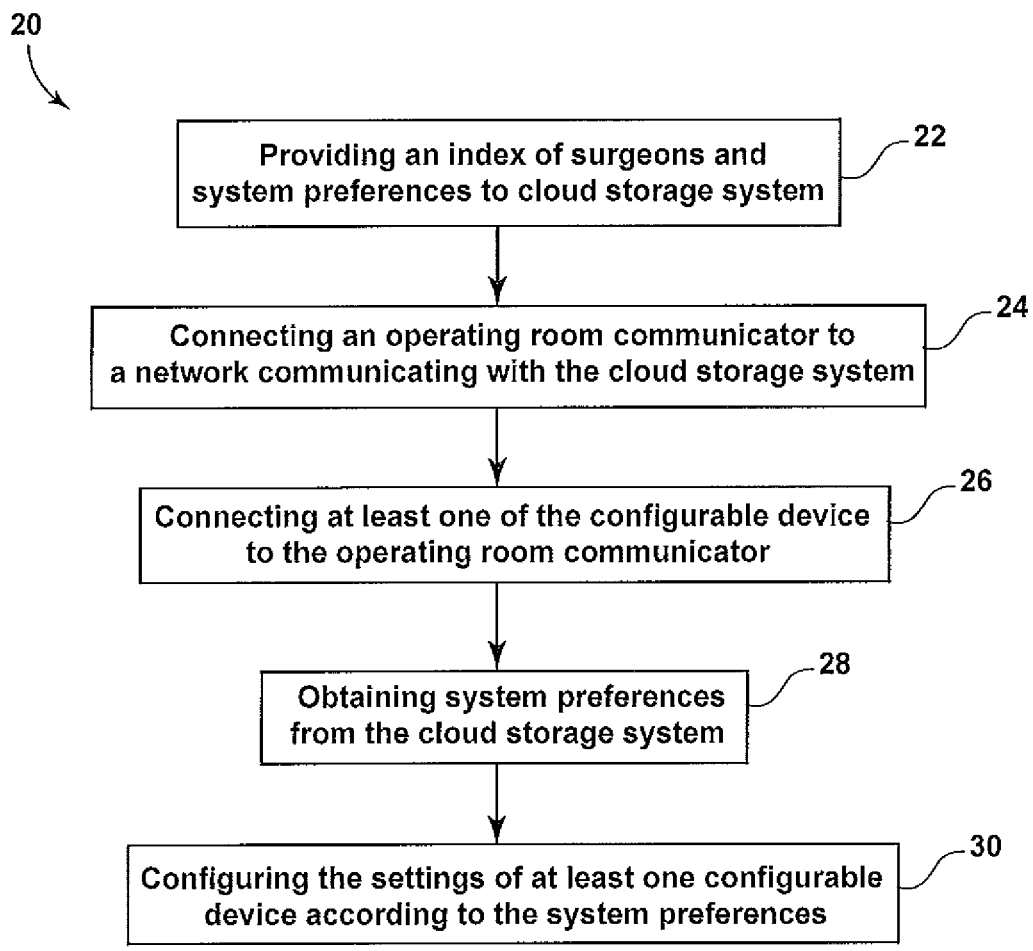
FIG. 3 illustrates a method of configuring the operating room using the system of FIG. 2.

FIG. 3 illustrates a method 20 of configuring the operating room 100 using the system of FIG. 2. First, the cloud storage system 12a having the index of surgeons and system preferences associated with each surgeon in the index of surgeons is provided at step 22. It is contemplated that the list of surgeons in the cloud storage system 12a could be entered according to name and/or AMA number (or other identifier). The operating room communicator 14 is connected to a network communicating with the cloud storage system 12a at step 24. At least one of the configurable devices 16 is connected (wired or wirelessly) to the operating room communicator 14 at step 26. A person in the operating room 100 then obtains system preferences associated with a particular surgeon listed in the index of surgeons from the cloud storage system 12a at step 28. The person in the operating room 100 can find the surgeon in the index of surgeons by looking up the surgeon's name and/or AMA number (or other identifier). The index of surgeons and the system preferences can be obtained from the cloud storage system 12a without logging into the cloud storage system 12a. In other words, anyone can access the index of surgeons and the system preferences from the cloud storage system 12a without identifying and/or authenticating the person obtaining the system preferences in step 28. Finally, settings of the at least one configurable device 16 are configured according to the system preferences associated with the particular surgeon at step 30. While the steps of the method 20 are presented in FIG. 3 in a particular order, the steps can be performed in any order or simultaneously, except that step 30 preferably occurs after the remaining steps.

Figure 4:
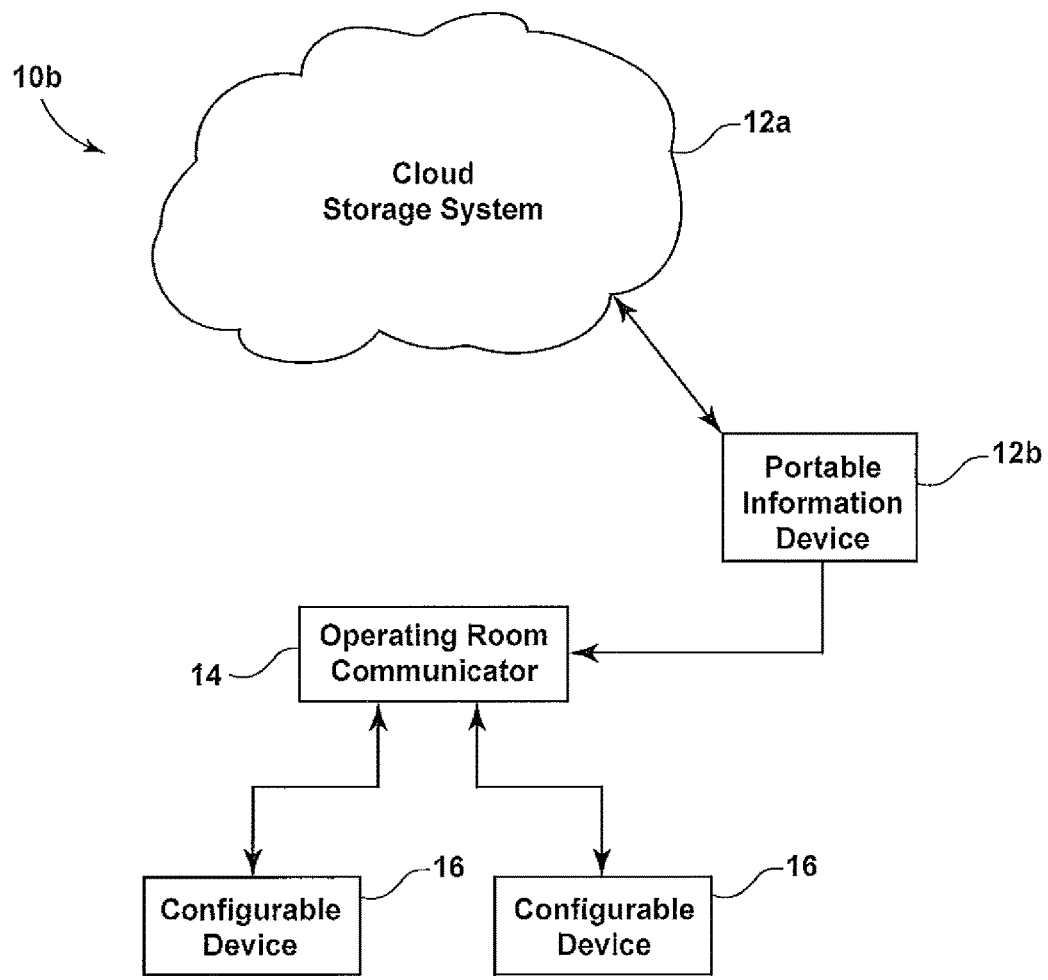
FIG. 4 illustrates a second embodiment of the system for configuring devices in the operating room, wherein the system preference storage system is a portable information device carried or worn by the surgeon.

FIG. 4 illustrates a second embodiment of the system 10b for configuring devices in the operating room 100, wherein the system preference storage system is a portable information device 12b (e.g., a tablet computer, a smartphone or an RFID chip) carried or worn by the surgeon. When the surgeon enters the operating room 100, the operating room communicator 14 automatically communicates with the portable information device 12b to obtain the system preferences. It is contemplated that the portable information device 12b could hold the system preferences within the memory thereof or that the portable information device 12b could communicate with the cloud storage system 12a (or other storage system) to obtain the system preferences. The system preferences include preferences for the settings of the configurable devices 16 in the operating room 100. The system preferences are obtained from the portable information device 12b automatically when a surgeon comes into proximity with the operating room communicator 14 without actively interacting with the operating room communicator 14.

Figure 5:
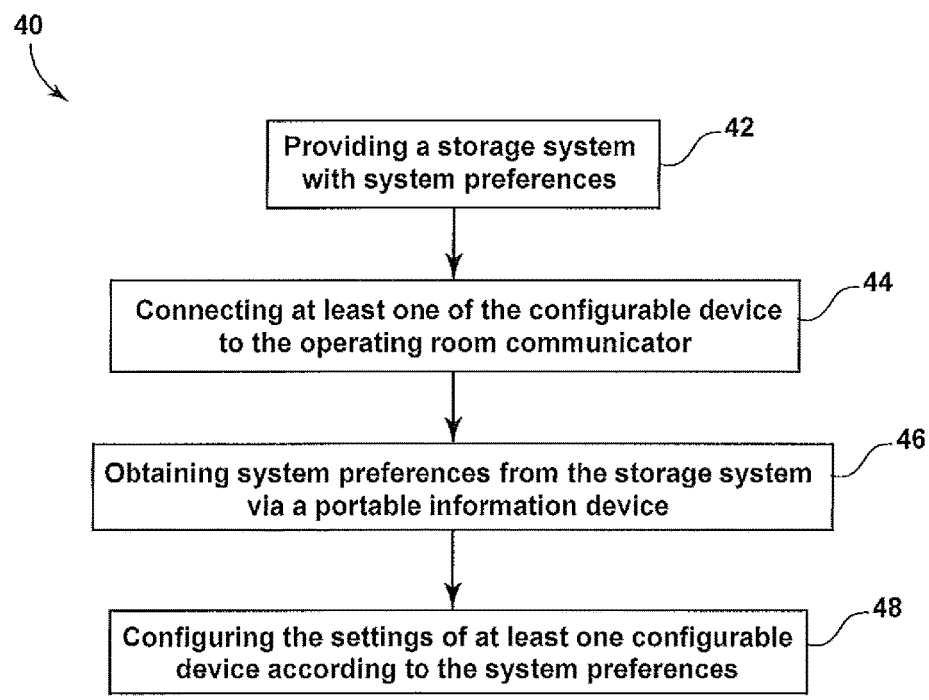
FIG. 5 illustrates a method of configuring the operating room using the system of FIG. 4.

FIG. 5 illustrates a method 40 of configuring the operating room 100 using the system of FIG. 4. First, the storage system 12 having system preferences is provided at step 42. As outlined above, the system preferences can be stored in the portable information device 12b or can be obtained from cloud storage system 12a (or other storage system) by the portable information device 12b. At least one of the configurable devices 16 is connected (wired or wirelessly) to the operating room communicator 14 at step 44. The system preferences are then obtained from the portable information device 12b at step 46. The system preferences are obtained from the portable information device 12b in step 46 automatically when a surgeon comes into proximity with the operating room communicator 14 without actively interacting with the operating room communicator 14. Methods of automatically obtaining the system preferences from the portable information device 12b are discussed below.

Finally, the settings of the at least one configurable device 16 are configured according to the system preferences at step 48. While the steps of the method 40 are presented in FIG. 5 in a particular order, the steps can be performed in any order or simultaneously, except that step 48 occurs after the remaining steps.

Figure 6:
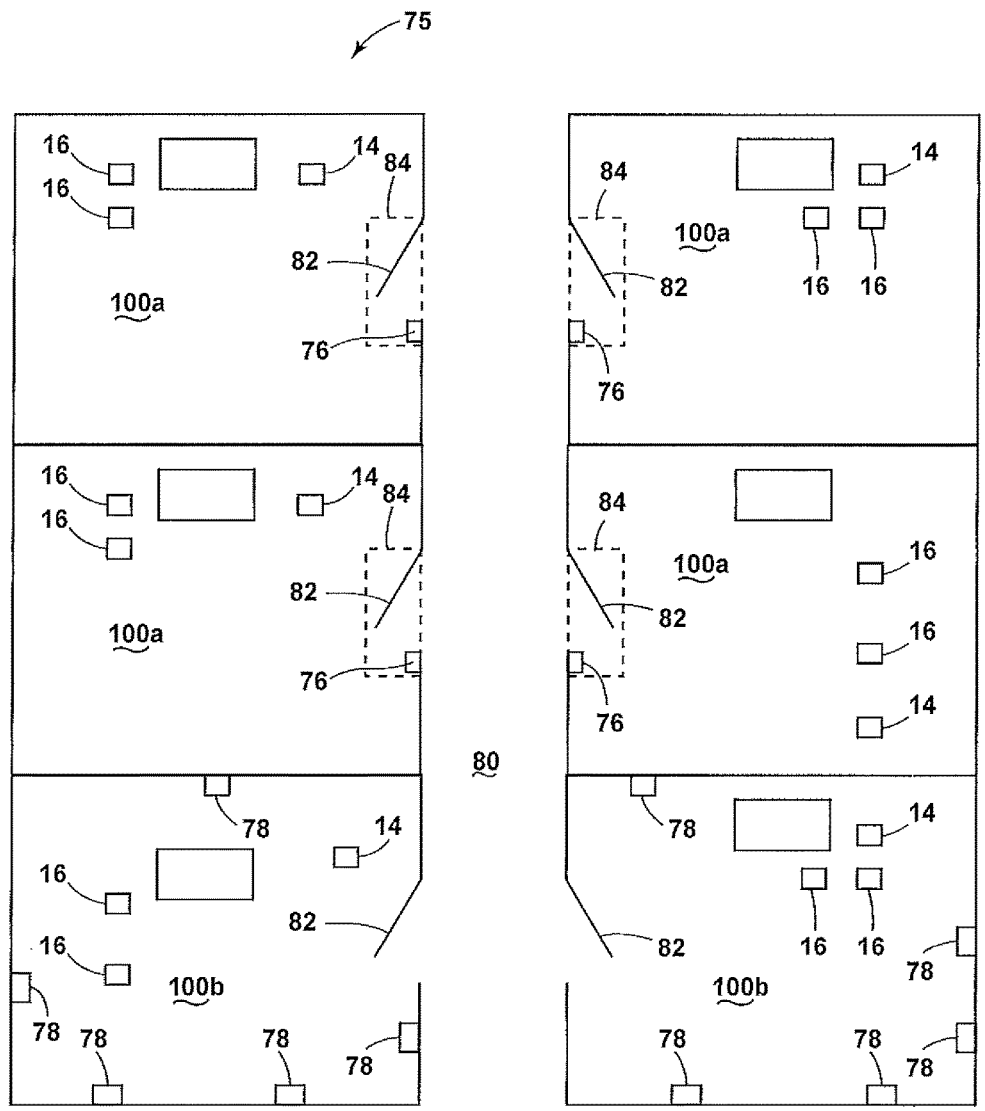
FIG. 6 illustrates a schematic view of a floor of a medical facility for illustrating two methods of automatically determining when a surgeon comes into proximity with an operating room communicator to configure the operating room using the method of FIG. 5.

FIG. 6 illustrates a schematic view of a floor 75 of a medical facility for illustrating two methods of automatically determining when a surgeon comes into proximity with the operating room communicator 14. The floor 75 of the medical facility includes a plurality of first operating rooms 100a that use a first method of automatically determining when a surgeon comes into proximity with the operating room communicator 14 and a plurality of second operating rooms 100b that use a second method of automatically determining when a surgeon comes into proximity with the operating room communicator 14. Each of the operating rooms 100a, 100b can be entered from a corridor or hallway 80 through a door or entryway 82.

The illustrated first operating rooms 100a are provided with a room monitor 76. In the illustrated example, the room monitor 76 is located adjacent the door or entryway 82. However, it is contemplated that the room monitor 76 could be located anywhere within the first operating room 100a. The room monitor can have a motherboard that includes one or more processors or other similar control devices as well as one or more memory devices. The processor controls the overall operation of the operating room communicator and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. Each room monitor 76 has a registration zone 84 in the first operating room 100a. For example, when the room monitor 76 is adjacent the door or entryway 82 connecting the first operating room 100a to the hallway 80, the registration zone 84 will be adjacent the door or entryway 82. However, the registration zone 84 could be located anywhere within the first operating room 100a depending on the location of the room monitor 76. The room monitor 76 will automatically link with the portable information device 12b when the portable information device 12b passes through the registration zone 84. The room monitor 76 can use infrared communication, near field communication, an RFID system, WiFI RSS readings or BlueTooth pairing (or similar systems) to automatically sense passage of the portable information device 12b through the registration zone 84. Once the room monitor 76 senses passage of the portable information device 12b through the registration zone 84, the room monitor 76 will instruct the operating room communicator 14 (via wired connection or wirelessly) to obtain the system preferences from the portable information device 12b. It is contemplated that the room monitor 76 could be located anywhere within the first operating room 100a such that the portable information device 12b only has to pass through the registration zone 84 at the room monitor 76 to automatically transmit the system preferences to the operating room communicator 14. Moreover, it is contemplated that the room monitor 76 could be integrated into the operating room communicator 14 such that the operating room communicator 14 will sense when the portable information device 12*b* passes through the registration zone 84 and will then automatically obtain the system preferences. Alternatively, it is contemplated that the portable information device 12*b* could include the room monitor 76 and the room monitor 76 automatically senses proximity of the operating room communicator 14 to transmit the system preferences to the operating room communicator 14.

The illustrated second operating rooms 100*b* are provided with a "time-of-flight" arrangement for determining that the portable information device 12*b* has entered the second operating room 100*b*. The second operating rooms 100*b* do not have a room monitor 76 located adjacent the door or entryway 82 thereof. Instead, the portable information device 12*b* relies on two or more transceiver locator devices 78, and for example at least five transceiver locator devices, provided within the second operating room 100*b* to determine the presence of the portable information device 12*b* in the second operating room 100*b*.

The time-of-flight embodiment with multiple transceiver locator devices 78 shown in FIG. 6 provides separate distance values from each of the respective transceiver locator devices 78 to the portable information device 12*b* by, for example, timing the sending of a specific signal to the portable information device 12*b* and determining the return time of a return signal from the portable information device 12*b*. In one embodiment, this information is then sent wirelessly to the operating room communicator 14. The operating room communicator 14 compiles the distance values for the portable information device 12*b* from the multiple transceiver locator devices 78 to determine if the portable information device 12*b* is in the second operating room 100*b*. If the operating room communicator 14 determines that the portable information device 12*b* is in the second operating room 100*b*, the operating room communicator 14 will then automatically obtain the system preferences from the portable information device 12*b*. Further, the exact location of the portable information device 12*b* can be determined by a central time-of-flight microcomputer or the like.

While the embodiment of FIG. 6 shows five transceiver locator devices 78 capable of identifying the presence of the portable information device 12*b* within the second operating room 100*b*, in another embodiment a fixed transceiver locator device 78 is mounted on each wall, along with the floor and ceiling. In this embodiment, the six transceiver locator devices 78 each measure respective distances from the portable information device 12*b*. The measured distances of the portable information device 12*b* from each of the six transceiver locator devices 78 are correlated to determine whether the portable information device 12*b* is in the second operating room 100*b*. In another embodiment, the time-of-flight location system operates to detect the presence of the portable information device 12*b* in the second operating room 100*b* according to the system disclosed in U.S. Pat. No. 5,661,490, the disclosure of which is hereby incorporated by reference in its entirety. It is contemplated that the operating rooms could include both the room monitor 76 and the transceiver locator devices 78, with either or both of these devices being used to determine that the portable information device 12*b* is in the operating room.

Figure 7:
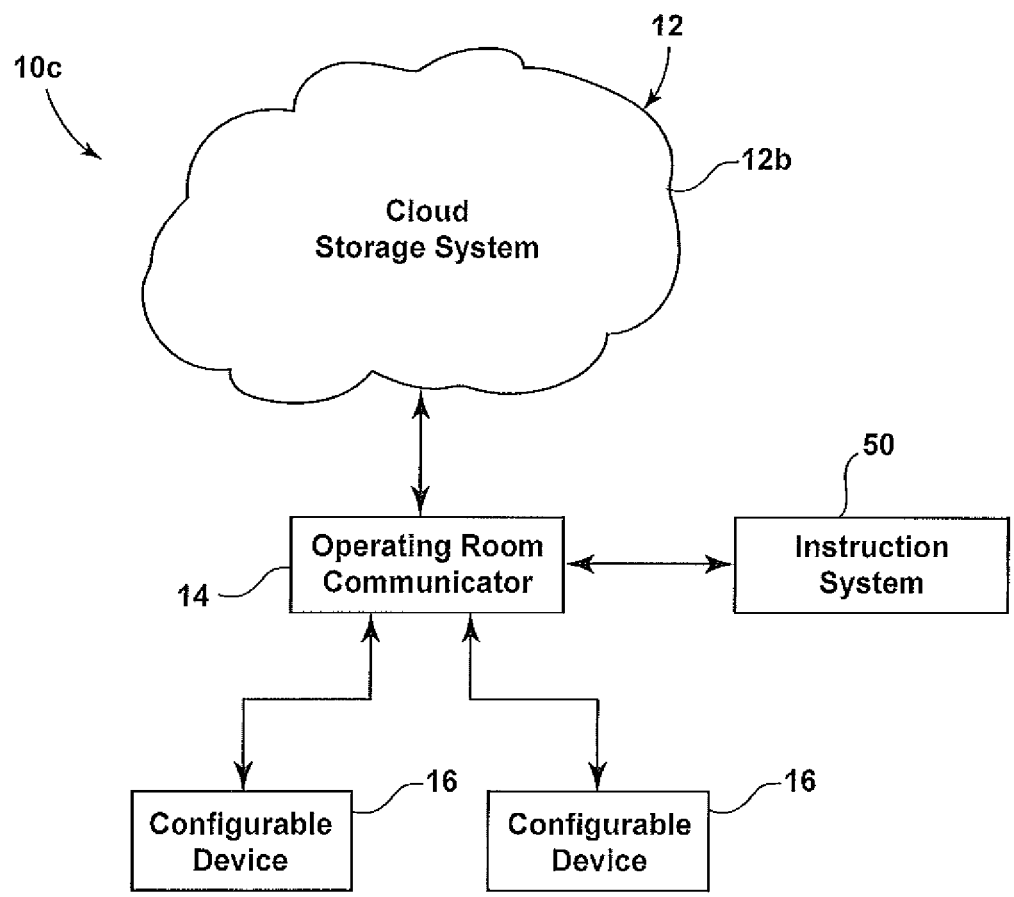
FIG. 7 illustrates a third embodiment of the system for configuring devices in the operating room.

FIG. 7 illustrates a third embodiment of the system 10*c* for configuring devices in the operating room 100, wherein the system preference storage system 12 can be a cloud storage system 12*a* or any other remote storage system. The operating room communicator 14 automatically obtains the preferences from the system preference storage system 12 when instructed to do so by an instruction system 50, wherein the instruction system 50 is remote from the operating room communicator 14. The instruction system 50 can be the portable information device 12*b* described above. Instead of having the portable information device 12*b* provide the system preferences to the operating room communicator 14 as outlined above in regard to FIGS. 5 and 6, the portable information device 12*b* instructs the operating room communicator 14 to obtain the system preferences from the system preference storage system 12. The portable information device 12*b* can send instructions to the operating room communicator 14 to obtain the system preferences by passing through the registration zone 84 of the room monitor 76 as discussed above. Furthermore, or alternatively, the instruction system 50 can communicate directly with the operating room communicator 14 using infrared communication, near field communication, an RFID system, WiFI RSS readings or BlueTooth pairing (or similar systems) to instruct the operating room communicator 14 to obtain the system preferences. The instruction system 50 can also use visual data to instruct the operating room communicator 14 to obtain the system preferences. For example, the instruction system 50 can be wearable technology worn by the surgeon. The wearable technology can include a camera that captures an image taken from the surgeon's point of view or perspective. The camera of the wearable technology of the instruction system 50 can read a bar code (or similar unique information) on the operating room communicator 14 or other item unique to a particular room, with the wearable technology sending a signal to the operating room communicator 14 (e.g., through a wireless network) to instruct the operating room communicator 14 to obtain the system preferences. An example of the wearable technology is Google Glass sold by Google Inc. of Mountain View, Calif. The instruction system 50 can also include a room camera 300 (see FIG. 9) that obtains an image of the surgeon, with the room camera 300 being connected to a processing system that identifies the surgeon and then sends a signal to the operating room communicator 14 (e.g., through a wireless network or via wired communication) to instruct the operating room communicator 14 to obtain the system preferences of that surgeon.

Figure 8:
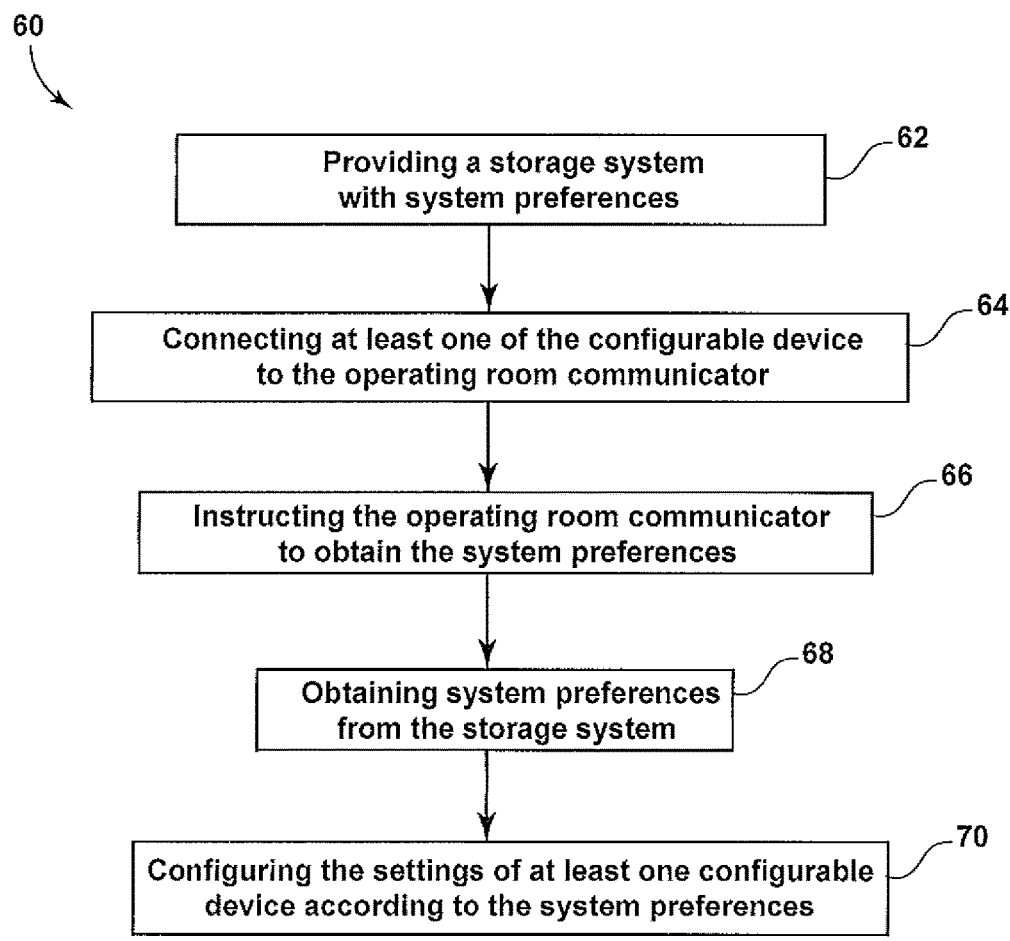
FIG. 8 illustrates a method of configuring the operating room using the system of FIG. 7.

FIG. 8 illustrates a method 60 of configuring the operating room 100 using the system of FIG. 7. First, the storage system 12 having system preferences is provided at step 62. At least one of the configurable devices 16 is connected (wired or wirelessly) to the operating room communicator 14 at step 64. The instruction system 50 instructs the operating room communicator 14 to obtain the system preferences from the storage system 12 at step 66. The operating room communicator 14 obtains the system preferences from the storage system 12 at step 68. Finally, the settings of the at least one configurable device 16 are configured according to the system preferences at step 70. While the steps of the method 60 are presented in FIG. 8 in a particular order, steps 62 and 64 can be performed in any order or simultaneously.

Figure 9:
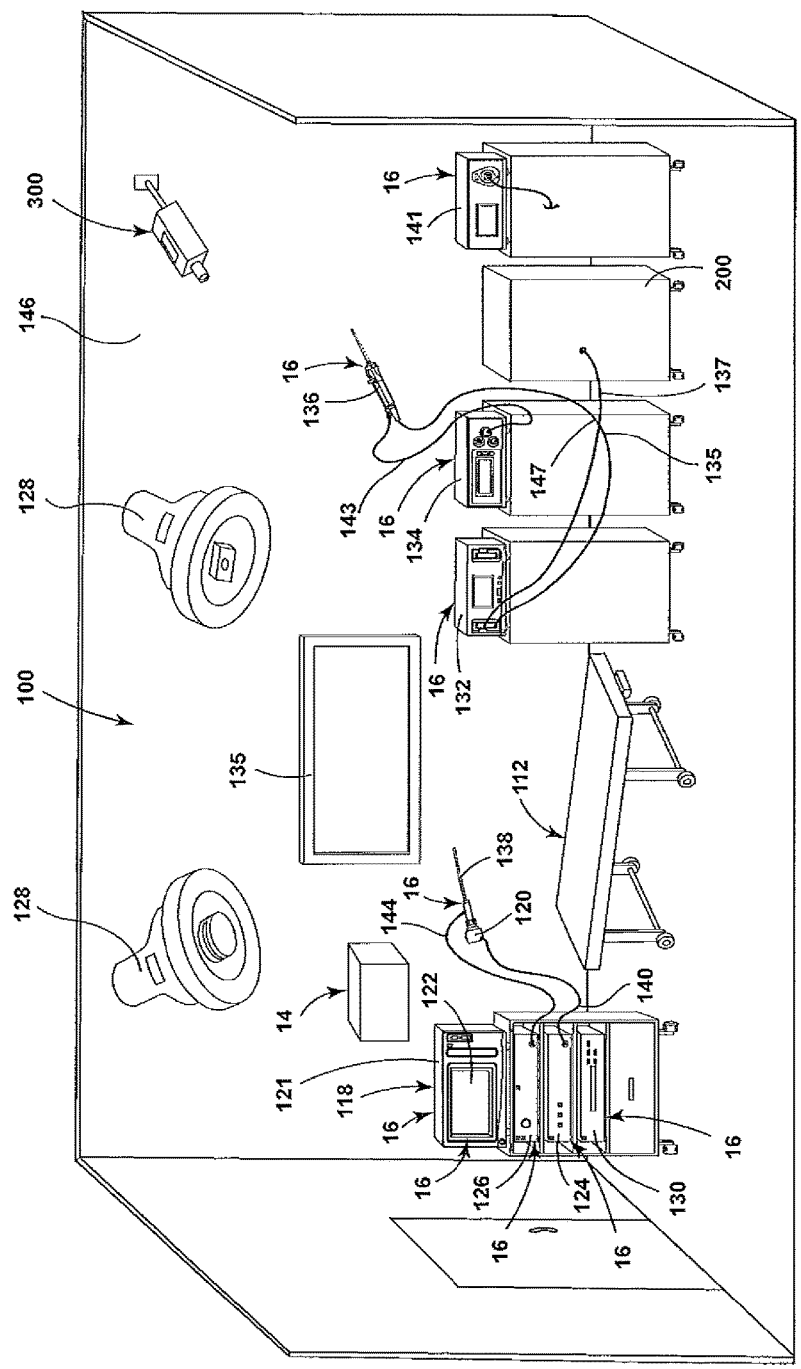
FIG. 9 is a perspective view of an operating room illustrating examples of configurable devices.

FIG. 9 depicts a perspective view of an operating room 100 according to one embodiment of the detailed description illustrating specific examples of the configurable devices 16. In the illustrated example, the plurality of configurable devices 16 may be devices which are not connected to a network, or may be devices which are incapable of being connected to a network, and instead are connected to the operating room communicator 14, which is connected to a network (wired or wirelessly). However, it is contemplated that some or all of the configurable devices 16 could be connected to a network. The operating room 100 includes a surgical table 112 configured to support a patient thereon during surgery and a plurality of the configurable devices 16 used for performing or assisting in surgery on the patient within the operating room 100. The settings of the configurable devices 16 in the operating room 100 are configured according to instructions received from the operating room communicator 14. Moreover, as outlined below, in the illustrated example, the operating room communicator 14 can also control the functions of the configurable devices 16 along with configuring the settings of the configurable devices 16. However, it is contemplated that the configurable devices 16 can also or alternatively be independently controlled.

As illustrated in FIG. 9, examples of configurable devices 16 include an image and video capture and recording device 118, a video camera 120 and an associated endoscope 138, a touchscreen monitor 122, a camera control unit 124, a scope light source unit 126, operating room lights 128, a printer 130, a fluid management pump 132, an insufflator 141, a shaver 136, an RF and shaver control 134 and an additional monitor 135. However, any configurable device 16 located within the operating room 100 can be configured from instructions received by the operating room communicator 14. The operating room communicator 14 receives the preferences for the settings for the configurable devices 16 from the system preference storage system 12, 12a, 12b as outlined above and then passes the preferences for the settings to the configurable devices 16 for configuring the settings of the configurable devices 16.

In the illustrated example, one of the configurable devices 16 is the image and video capture and recording device 118 located in a control housing 121. The image and video capture and recording device 118 can output images and video on the touchscreen monitor 122, which can be integrated into the control housing 121. The image and video capture and recording device 118 can also output images and video to the additional monitor 135 via either a wired connection or wirelessly. The illustrated image and video capture and recording device 118 is therefore capable of displaying images and videos on the touchscreen monitor 122 and/or on the additional monitor 135 captured live by cameras and/or replayed from recorded images and videos. The image and video capture and recording device 118 can also control the images and videos being shown on the touchscreen monitor 122 (e.g., by controlling the source of the image on the touchscreen monitor 122 (e.g., from a camera, from a saved video file, etc.)).

The illustrated image and video capture and recording device 118 is also capable of recording images and videos. The image and video capture and recording device 118 can include an internal hard drive for storing captured images and videos and can also communicate with a picture archiving and communication system (PACS), as is well known to those skilled in the art, to save images and video in the PACS and for retrieving images and videos from the PACS. The image and video capture and recording device 118 can also display any saved images (e.g., from the internal hard drive or from the PACS) on the touchscreen monitor 122 and/or the additional monitor 135. It is contemplated that the image and video capture and recording device 118 could obtain or create images of a patient during a surgical procedure from a variety of sources (e.g., from video cameras, video cassette recorders, X-ray scanners (which convert X-ray films to digital files), digital X-ray acquisition apparatus, fluoroscopes, CT scanners, MRI scanners, ultrasound scanners, CCD devices, and other types of scanners (handheld or otherwise)).

The illustrated operating room communicator 14 can adjust settings of the image and video capture and recording device 118. For example, the operating room communicator 14 can adjust the settings of the type of encryption for the images and videos recorded by the image and video capture and recording device 118, can change a save location of images and videos captured by the image and video capture and recording device 118 (e.g., on a connected Ipad®, onto a CD or DVD or a particular location on a network (e.g., DICOM)), can change a recording format (e.g., MPEG 2, MPEG 2 HD, MPEG 4, AVC, HEVC), can change a resolution record bitrate (e.g., high or low), and can change a video capture format (e.g., standard single picture or picture-in-picture) and/or can change any other setting of the image and video capture and recording device 118. The illustrated operating room communicator 14 can also configure the settings of the touchscreen monitor 122 to adjust the output image shown on the touchscreen monitor 122 (e.g., by changing resolution or showing picture-in-picture videos). Similarly, the operating room communicator 14 can configure the settings of the additional monitor 135 to adjust the output image shown on the additional monitor 135 (e.g., by changing resolution or showing picture-in-picture videos). The image and video capture and recording device 118 having the touchscreen monitor 122 within the control housing 121 is well known to those skilled in the art. An example of an image and video capture and recording device 118 is the SDC3 HD Information Management System (with device control) as sold by Stryker Corporation of Kalamazoo, Mich. An example of an additional monitor 135 is the WISE HDTV wireless display as sold by Stryker Corporation of Kalamazoo, Mich. The additional monitor 135 can be wired to the image and video capture and recording device 118 or can be wirelessly connected (e.g., by using the Wireless WISE HD transmitter as sold by Stryker Corporation of Kalamazoo, Mich.).

In the illustrated example, several of the configurable devices 16 can be controlled by the image and video capture and recording device 118 for obtaining the images and videos and for outputting the captured and recorded images and videos. For example, the images and videos can be captured by the video camera 120, which includes well-known components for generating color video based on light received through a scope 138 of the type commonly used for laparoscopy or arthroscopy (e.g., endoscope). The image and video capture and recording device 118 can control the video camera 120 to turn on and turn off the video camera 120 or to capture images using the video camera 120. The operating room communicator 14 can communicate with the video camera 120 to adjust settings of the video camera 120 (e.g., resolution, zoom, etc.)

Yet another configurable device is the camera control unit 124 that is coupled to the video camera 120 by a flexible electronic transmission line 140. The operating room communicator 14 can adjust settings of the video camera 120 at the video camera 120 itself or through the camera control unit 124 (e.g., adjusting the video camera 120 to settings according to a surgery being performed, settings of programmable buttons on the video camera 120, etc.). The transmission line 140 conveys video data from the video camera 120 to the camera control unit 124 and also conveys various control signals bi-directionally between the video camera 120 and the camera control unit 124. The camera control unit 124 can be connected (wired or wirelessly) to the image and video capture and recording device 118 to provide the images and videos to the image and video capture and recording device 118. Video cameras 120 and camera control units 124 used with scopes 138 are well known to those skilled in the art. An example of the video camera 120 and camera control unit 124 for use with an endoscope is the 1488 HD Camera as sold by Stryker Corporation of Kalamazoo, Mich.

Another configurable device 16 is the light source unit 126 that transmits high intensity light into the patient through the scope 138 via a fiber optic cable 144. The operating room communicator 14 can configure settings of the light source unit 126 (e.g., adjusting intensity and wavelength of light emitting from the light source unit 126). Light source units 126 used with scopes 138 are well known to those skilled in the art. An example of the light source unit 126 for use with the endoscope 138 is the L9000 LED Light Source as sold by Stryker Corporation of Kalamazoo, Mich.

Another of the plurality of configurable devices 16 can include the operating room lights 128 mounted to one of the ceiling, a room wall 146 or other stationary structure of the operating room 100. The operating room communicator 14 can configure the setting of the operating room lights 128 (e.g., the intensity of the operating room lights 128). The operating room communicator 14 can also be used to adjust the intensity of the operating room lights 128.

Yet another one of the plurality of configurable devices 16 is the printer 130. The printer 130 can be connected to the image and video capture and recording device 118 for outputting images from the image and video capture and recording device 118. The operating room communicator 14 can configure the setting of the printer 130 (e.g., page layout, color, etc.). The operating room communicator 14 can also control the printer 130 in order to print selected images. An example of the printer 130 is the SDP1000 Medical Grade Digital Printer as sold by Stryker Corporation of Kalamazoo, Mich.

Another of the plurality of configurable devices 16 is the fluid management pump 132. The fluid management pump 132 is employed during surgical procedures to introduce sterile solution into surgical sites and to remove fluid and debris generated by the procedure. In the illustrated example, the fluid management pump 132 can supply the motive force for pumping the sterile solution through an inflow tube (not shown) into the surgical site via a cannula. The fluid management pump 132 can also supply the motive force for suctioning solution and any waste material removed from the surgical site from an outflow tube 147 to a waste tube 137 connected to a waste container 200. In the illustrated example, the outflow tube 147 is connected to the shaver 136. An example of the fluid management pump is disclosed in U.S. Patent Application Publication No. 2013/0267779 entitled CONTROL FOR SURGICAL FLUID MANAGEMENT PUMP SYSTEM, the entire contents of which are hereby incorporated herein by reference. The operating room communicator 14 can configure the settings of the fluid management pump 132 by setting various controls of the control unit for the fluid management pump 132. For example, the operating room communicator 14 can set the pressure of the fluid being pumped into the surgical site and/or the flow rate of fluid to or from the surgical site. The operating room communicator 14 can also set the settings of the shaver 136 by setting the speed of the shaver or other settings. An example of the shaver 136 is the Formula® Shaver Hand Piece as sold by Stryker Corporation of Kalamazoo, Mich. The operating room communicator 14 can also be used to control the fluid management pump 132 by altering various controls of the control unit for the fluid management pump 132. For example, the operating room communicator 14 can control the pressure of the fluid being pumped into the surgical site and/or the flow rate of fluid to or from the surgical site. The operating room communicator 14 can also control the speed of the shaver 136 or other settings.

Yet another one of the plurality of configurable devices 16 is the RF and shaver control 134. The RF and shaver control 134 sends power to an ablation and coagulation device or electrosurgical tool (not shown) and/or the shaver 136. Ablation and coagulation devices are well known to those skilled in the art. An example of an ablation and coagulation device that can be connected to the RF and shaver control 134 is SERFAS™ Energy Probe as sold by Stryker Corporation of Kalamazoo, Mich. The RF and shaver control 134 sends power to the shaver 136 through a cable 143. The operating room communicator 14 can configure the settings of the RF and shaver control 134 by setting the power sent to the ablation and coagulation device (not shown) and/or the shaver 136 or other settings. An example of the RF and shaver control 134 is the Crossfire® arthroscopic resection system as sold by Stryker Corporation of Kalamazoo, Mich. The operating room communicator 14 can also control the RF and shaver control 134 by altering the power sent to the ablation and coagulation device (not shown) and/or the shaver 136 or other controls.

Another of the plurality of configurable devices 16 is the insufflator 141. The insufflator 141 is used to supply inert, nontoxic gases, such as carbon dioxide, into a body cavity, in order to expand the cavity, or to minimize visual obstruction during minimally invasive or laparoscopic surgery. An insufflator 141 is well known to those skilled in the art. The operating room communicator 14 can configure the settings of the insufflator 141 by setting the pressure to be sent to the body cavity or other settings. An example of the insufflator 141 is the PNEUMOSURE® 45L Insufflator as sold by Stryker Corporation of Kalamazoo, Mich. The operating room communicator 14 can also control the insufflator 141 by adjusting the pressure of the gas supplied into the body cavity.

The operating room communicator 14 can have a motherboard that includes one or more processors or other similar control devices as well as one or more memory devices. The processor controls the overall operation of the operating room communicator and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. The operating room communicator 14 can also have a network interface for connecting the operating room communicator 14 to the Internet or other type of wide area network (WAN), a local area network (LAN), a corporate intranet, any other type of network, or a combination of such networks. The operating room communicator 14 can also be connected to the system preference storage system 12, 12a as discussed above.

The illustrated operating room communicator 14 can be a stand-alone device communicating with the configurable devices 16 (wired or wirelessly) to control the configurable devices 16 and to configure the configurable devices 16 by adjusting the settings of the configurable devices 16. Alternatively, the operating room communicator 14 can be incorporated into one of the configurable devices 16 that communicates with the other configurable devices 16 to control the other configurable devices 16 and to configure the configurable devices 16 by adjusting the settings of the configurable devices 16. In the illustrated example, the operating room communicator 14 can be incorporated within the control housing 121 of the image and video capture and recording device 118 such that the touchscreen monitor 122 can be used to control the configurable devices 16. It is further contemplated that the image and video capture and recording device 118 can receive audible or voice commands to control the configurable devices 16.

In the illustrated example, the system preferences can initially have default settings for every user, with the default settings saved in the system preference storage system 12, 12*a*, 12*b* until changed. The user, such as a sales representative or other user can then adjust the settings for the user and save the altered settings in the system preference storage system 12, 12*a*, 12*b*. It is contemplated that the settings saved in the system preference storage system 12, 12*a*, 12*b* in association with one user profile can be copied and saved to another user profile without anyone logging into the system preference storage system 12, 12*a*, 12*b*. Furthermore, the system preference storage system 12, 12*a*, 12*b* can be set for various specialties (e.g., podiatry, orthopedics, etc.), general surgeries (e.g., laparoscopy, arthroscopy, cystoscopy; microscopy, hysteroscopy, etc.) or particular surgical procedures (e.g., distal clavicle repair, ACL reconstruction, etc.). Furthermore, it is contemplated that the operating room communicator 14 can have a settings save function to allow settings to be uploaded or saved to the system preference storage system 12, 12*a*, 12*b* if changed during use of the configurable devices 16. It is also contemplated that the preferences could be used for an operative note template as disclosed in U.S. Patent Application No. 62/061,398 entitled INTRA-SURGICAL DOCUMENTATION SYSTEM, the entire contents of which are hereby incorporated herein by reference. Moreover, it is contemplated that software updates for the configurable devices 16 could also be received by the configurable devices 16 along with the preferences for the settings of the configurable devices 16 as discussed herein.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of configuring an operating room comprising:
   providing a cloud storage system having system preferences;
   providing the cloud storage system with an index of surgeons;
   associating each of the system preferences with at least one surgeon in the index of surgeons;
   providing an operating room communicator;
   connecting at least one configurable device to the operating room communicator;
   obtaining the system preferences from the cloud storage system; and
   automatically configuring settings of the at least one configurable device according to the system preferences;
   wherein the system preferences are obtained without logging into the cloud storage system.

2. The method of configuring the operating room of claim 1, further including:
   altering the settings of the at least one configurable device; and
   saving the altered settings as a new version of the system preferences in the cloud storage system.

3. The method of configuring the operating room of claim 1, wherein:
   the index of surgeons includes a list of American Medical Association surgeon identification numbers and each one of the American Medical Association surgeon identification numbers has the system preferences associated therewith.

4. The method of configuring the operating room of claim 1, wherein:
   the index of surgeons includes a list of surgeons' names and each one of the surgeons' names has the system preferences associated therewith.

5. The method of configuring the operating room of claim 1, further including:
   providing an instruction system; and
   instructing the operating room communicator to obtain the system preferences with the instruction system.

6. The method of configuring the operating room of claim 5, wherein:
   the instruction system comprises a vision system that recognizes a visual cue in the operating room to thereby instruct the operating room communicator to obtain the system preferences when the vision system recognizes the visual cue.

7. The method of configuring the operating room of claim 6, wherein:
   the visual cue is a bar code in the operating room.

8. The method of configuring the operating room of claim 6, wherein:
   the visual cue is a surgeon in the operating room.

9. A method of configuring an operating room comprising:
   providing a cloud storage system having an index of surgeons and system preferences, with each of the system preferences being associated with at least one surgeon in the index of surgeons;
   providing an operating room communicator connected to a network communicating with the cloud storage system;
   connecting at least one configurable device to the operating room communicator;
   obtaining the system preferences associated with a particular surgeon listed in the index of surgeons from the cloud storage system; and
   automatically configuring settings of the at least one configurable device according to the system preferences associated with the particular surgeon;
   wherein the system preferences associated with the particular surgeon can be obtained without logging into the cloud storage system.

10. The method of configuring the operating room of claim 9, further including:
    altering the settings of the at least one configurable device; and
    saving the altered settings as a new version of the system preferences.

11. The method of configuring the operating room of claim 9, wherein:

the index of surgeons includes a list of American Medical Association surgeon identification numbers and each one of the American Medical Association surgeon identification numbers has the system preferences associated therewith.

12. The method of configuring the operating room of claim 9, wherein:
the index of surgeons includes a list of surgeons' names and each one of the surgeons' names has the system preferences associated therewith.

13. A method of configuring configurable devices in operating rooms in two separate facilities, the method comprising:
providing a cloud storage system having system preferences, the cloud storage system not being located at the separate facilities;
providing the cloud storage system with an index of surgeons;
associating each of the system preferences with at least one surgeon in the index of surgeons;
providing an operating room communicator for at least one operating room in each of the separate facilities;
communicating between at least one configurable device and each operating room communicator in the operating room in each of the separate facilities;
obtaining the system preferences from the cloud storage system; and
configuring settings of the at least one configurable device in the operating room in each of the separate facilities according to the system preferences;
wherein the system preferences are obtained without logging into the cloud storage system; and
wherein one of the system preferences can be used to configure the at least one configurable device in the operating room in each of the separate facilities.

14. The method of configuring configurable devices in operating rooms in two separate facilities of claim 13, further including:
altering the settings of the at least one configurable device; and
saving the altered settings as a new version of the system preferences in the cloud storage system.

15. The method of configuring configurable devices in operating rooms in two separate facilities of claim 13, wherein:
the index of surgeons includes a list of American Medical Association surgeon identification numbers and each one of the American Medical Association surgeon identification numbers has the system preferences associated therewith.

16. The method of configuring configurable devices in operating rooms in two separate facilities of claim 13, wherein:
the index of surgeons includes a list of surgeons' names and each one of the surgeons' names has the system preferences associated therewith.

* * * * *